United States Patent [19]
McEachern

[11] 4,084,318
[45] Apr. 18, 1978

[54] STABILIZED DENTAL IMPLANT

[76] Inventor: Charles M. McEachern, 3114 Old Canton Rd., Jackson, Mich. 39216

[21] Appl. No.: 459,373

[22] Filed: Apr. 9, 1974

[51] Int. Cl.² ............................................ A61C 13/22
[52] U.S. Cl. ...................................................... 32/10 A
[58] Field of Search ........................................ 32/10 A

[56] References Cited

U.S. PATENT DOCUMENTS

| 3,436,826 | 4/1969 | Edelman | 32/10 A |
| 3,474,537 | 10/1969 | Christensen | 32/10 A |
| 3,919,772 | 11/1975 | Lenczycki | 32/10 A |

Primary Examiner—Robert Peshock
Attorney, Agent, or Firm—Clarence A. O'Brien; Harvey B. Jacobson

[57] ABSTRACT

An intraosseous implant in which a rectangular anchor base is laterally inserted into a cavity cut into the mandible from one side. The cavity receives a portion of a drilling guide through which a drilling tool is directed to form a bore extending from the occlusal edge of the mandible through the cavity. A shank inserted through the bore is threadedly connected to the anchor base and to an anchor post for an artificial tooth in contact with the occlusal edge of the mandible.

4 Claims, 11 Drawing Figures

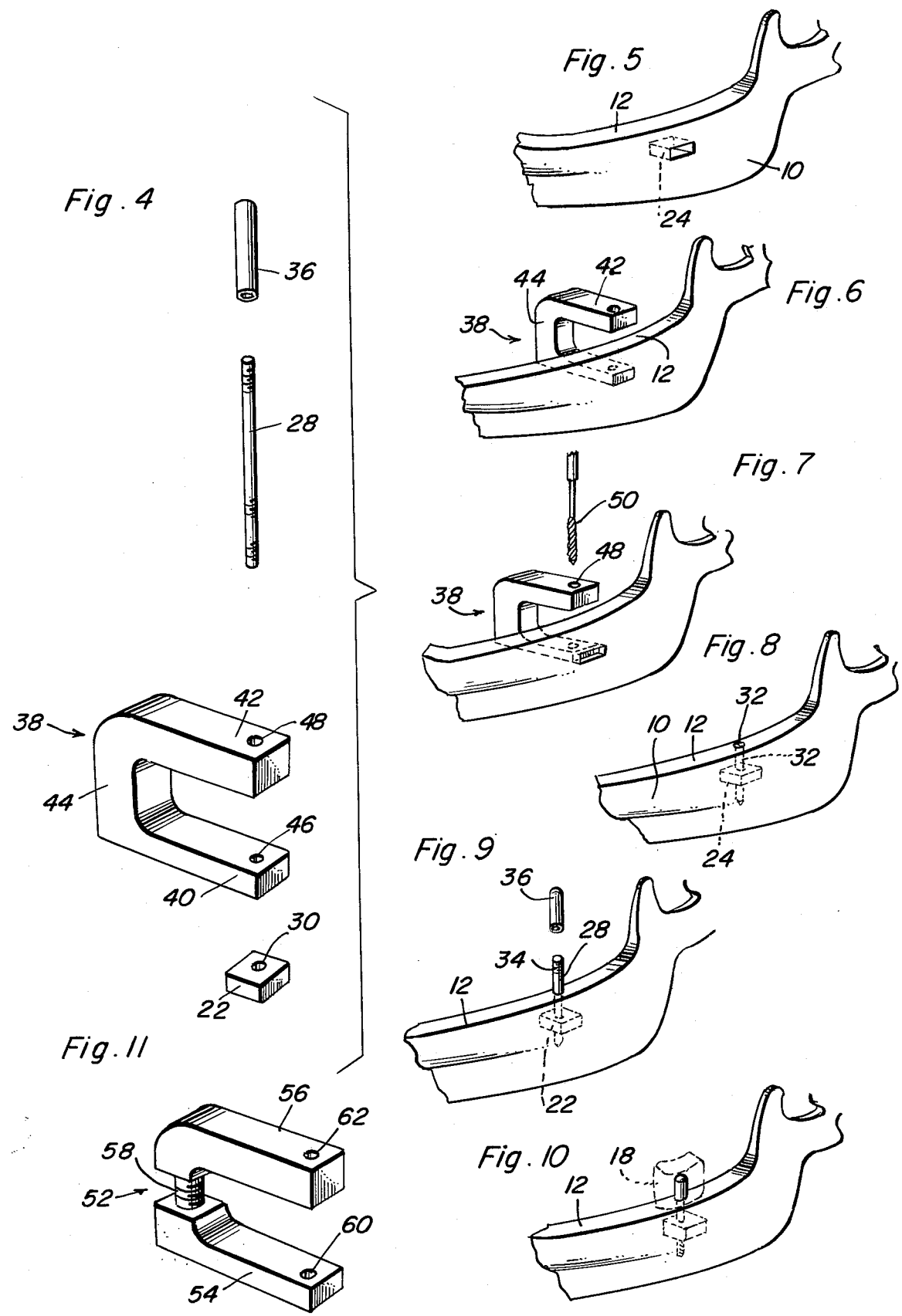

4,084,318

STABILIZED DENTAL IMPLANT

Examples of such prior implants are disclosed in U.S. Pat. Nos. 2,745,180, 2,857,670, 3,474,537, 3,623,226 and 3,708,883.

This invention relates to the implantation of an anchor for an artificial tooth in the jaw bone structure of a patient.

The anchoring of artificial teeth on the occlusal ridge of the mandible by implantation of an anchor in the bone structure, is well known. Such implants will sometimes fail after a certain amount of service because of epithealial infarction. Other causes of failure arise from tongue action of the patient, occlusal stress and lateral excursions and because of sticky foods pulling the implant loose. Failure sometimes also occurs because of the katabolic processes that breakdown the bone structure on the crest of the ridge following bone surgery. As a result of the possibility of failure because of the possible causes aforementioned, the use of implants in connection with artificial teeth, is sometimes a choice of last resort. It is therefore an important object of the present invention to provide a more satisfactory implant procedure to anchor artificial teeth in the mandible which will reduce or elimininate failure arising from the aforementioned causes.

In accordance with the present invention, a cavity is cut into the upper or lower jaw bone from a buccal or lingual side in spaced relation below the portion of the occlusal ridge on which an artificial tooth is to be anchored. A bore is then drilled vertically into the bone structure from the occlusal ridge intersecting the cavity. The cavity is shaped to receive an anchor base that is non-circular in cross section both along the axis of the bore and perpendicular thereto so as to resist any torsional strains applied to a shank that is inserted through the bore and threadedly connected to the anchor base. An anchor post is threadably mounted on the external portion of the inserted shank projecting from the occlusal ridge with which the post is in engagement. The foregoing arrangement precludes removal of the anchor assembly in a direction along the longitudinal axis of the shank or in any transverse direction. Further, the threaded connection of the post to the projecting portion of the shank enhances stabilization and resists torsional and vertical stresses.

Drilling of the bore aforementioned in an accurate manner is made possible by use of a drilling guide that is inserted into the lateral cavity. Spaced guide holes are accordingly formed in the drilling guide both in the portion inserted into the cavity and in a portion overlying the occlusal ridge into which the drilling tool penetrates. The bore is thereby drilled centrally through the cavity so that the shank may be positioned within the bore in alignment with a threaded hole formed in the anchor base that is inserted into the cavity.

These together with other objects and advantages which will become subsequently apparent reside in the details of construction and operation as more fully hereinafter described and claimed, reference being had to the accompanying drawings forming a part hereof, wherein like numerals refer to like parts throughout.

FIG. 4 is a perspective view showing the disassembled parts of an anchor assembly and drilling guide constructed in accordance with the present invention.

FIGS. 5 through 10 are perspective views showing the various steps in the installation of an anchor assembly in accordance with the present invention.

FIG. 11 is a perspective view of a modified form of drilling guide capable of being utilized for the present invention.

Figure 1:
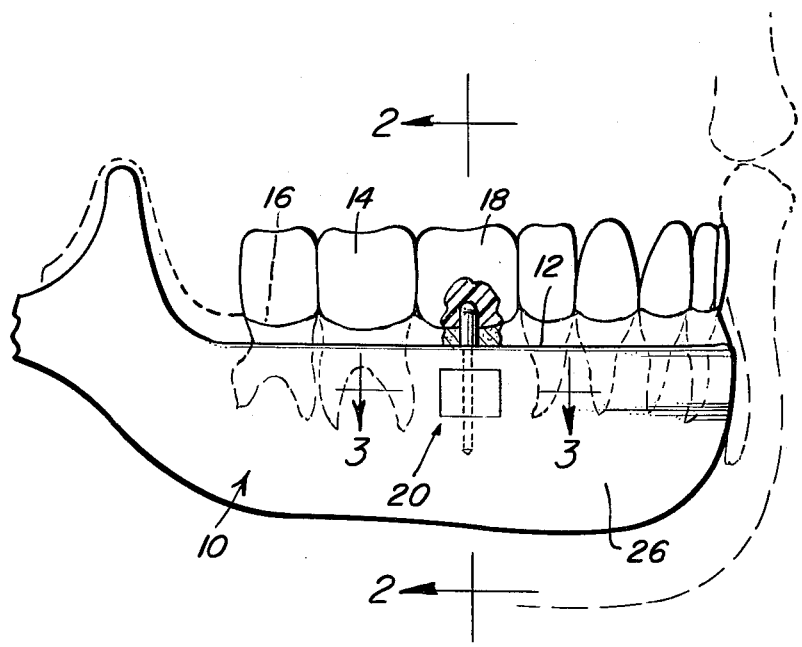
FIG. 1 is a side elevational view of a patient's jaw bone or mandible in which natural teeth are mounted as well as an artificial tooth anchored in accordance with the present invention.

Referring now to the drawings in detail, and initially to FIG. 1, a typical mandible or lower jaw bone 10 is shown having an occlusal ridge 12 on which a plurality of natural teeth 14 are supported above the epithealial 16 shown by dotted line. Also supported on the occlusal ridge 12, is an artificial tooth 18. The artificial tooth is secured to the mandible by an anchor assembly generally referred to by reference numeral 20.

Figure 2:
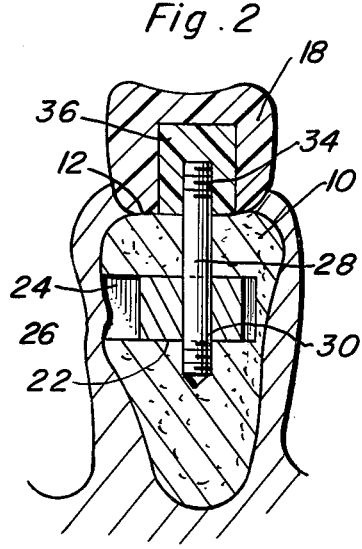
FIG. 2 is an enlarged transverse sectional view through the artificial tooth shown in FIG. 1 taken substantially through a plane indicated by section line 2—2 in FIG. 1.
Figure 3:
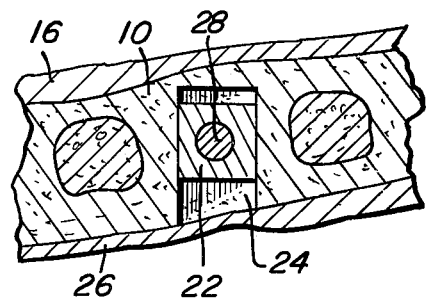
FIG. 3 is a top sectional view taken substantially through a plane indicated by section line 3—3 in FIG. 1.

Referring now to FIGS. 1, 2 and 3, the anchor assembly 20 includes a rectanglar anchor base 22 which is implanted within a rectangular cavity 24 cut into the mandible 10 from the lingual side 26 in spaced relation below the portion of the occlusal ridge 12 on which the artificial tooth 18 is supported. The base 22 is rectangular in cross section along a longitudinal axis of a threaded shank or fastener 28 to which it is threadedly connected. A threaded opening 30 is accordingly formed in the base 22 for this purpose which is adapted to be aligned with a vertical bore 32 formed in the mandible and extending from the occlusal ridge 12 in perpendicular intersecting relationship to the cavity 24. The rectangular shape of the base 22 and the cavity 24 into which it is inserted, will resist torsional displacement about the longitudinal axis of the shank 28 while the rectangular cross section of the base in a direction perpendicular to the longitudinal axis of the shank will resist any angular excursions in other directions.

The shank 28 includes an external threaded portion 34 onto which an anchor post or support 36 is threadedly mounted in contact with the occlusal ridge 12 thereby enhancing stabilization of the anchor assembly. The artificial tooth 18 is secured to the anchor post 36 in a manner well known to those skilled in the art.

Referring now to FIGS. 5 through 10, the procedure for implanting the anchor assembly is illustrated. FIG. 5 shows the mandible 10 with the rectangular cavity 24 laterally cut into the mandible in spaced relation below the occlusal ridge 12. It will be appreciated, that this cavity is cut by well known bone surgical techniques after the lingual side of the mandible bone surface is exposed at the proper location by incision and parting of the covering epiderm. A drilling guide generally referred to by reference numeral 38 is then utilized as shown in FIG. 6. The drilling guide is of generally U-shaped configuration having a leg portion 40 dimensioned to be inserted into the cavity 24, a thicker leg portion 42 spaced from the leg portion 40 by a bridging portion 44. The leg portions 40 and 42 are provided with aligned guide holes 46 and 48. When the leg portion 40 is inserted into the cavity 24, the leg portion 42 will be in overlying relationship to the portion of the occlusal ridge 12 at which the artificial tooth is to be located. A drilling tool 50 as shown in FIG. 7 may then be aligned and guidingly directed by means of the guide holes 48 and 46 in order to drill the bore 32 aforementioned as shown in FIG. 8. The anchor base 22 and shank 28 are then respectively inserted into the cavity 24 and bore 32 as shown in FIG. 9 after which the anchor post 36 is threadedly mounted on the external portion 34 of the shank by being screwed into engagement with the occlusal ridge 12 as shown in FIG. 10. The implantation procedure may be completed by suturing the epiderm over the cavity 24.

The size and location of the cavity 24 is selected in order to accommodate a base 22 which will provide the requisite support for the anchoring assembly. Further, the cavity 24 is located so as to avoid any nerve. The drilling guide must of course be dimensioned so as to fit within the mouth of the patient during the implantation procedure and also have its leg portion fit the cavity into which it is to be inserted. The other leg portion must also be spaced a proper distance in order to overlie the occlusal ridge and fit in the space to be occupied by the artificial tooth. Since there may be some variation in the spacing between the leg portions, as well as other dimensional variations, various size drilling guides 38 may be utilized. In FIG. 11, an adjustable drilling guide 52 is shown wherein the leg portion 54 inserted into the cavity is adjustably spaced from the other leg portion 56 by means of a threaded connector 58. The drilling guide 52 is otherwise the same as the drilling guide 38 and includes aligned guide holes 60 and 62 in the leg portions. The drilling guide will not only ensure that the bore 32 formed in the mandible extends through the cavity so as to appropriately locate the base 22 therein but will also be perpendicular to the base 22.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A method of attaching dental appliances to the jawbone of a user comprising the steps of: forming a first hole transversely through the jawbone; inserting a drill jig into said first hole to establish a guide axis through the jawbone intersecting said first hole; drilling a second hole in the jawbone along said guide axis; withdrawing the drill jig from the first hole; inserting an anchor element into the first hole, said anchor element having a length less that that of the first hole and a transverse bore adapted to be axially aligned with the second hole; inserting a fastener to which a dental appliance is secured at one end through said second hole and the bore in the inserted anchor element; and securing the fastener to the jawbone independently of the anchor element.

2. The method of claim 1 wherein said drill jig includes spaced drill guides, one of which is received in the first hole while the other overlies the jawbone and a frame connected to the drill guides in bridging relation to the jawbone.

3. The method of claim 2 wherein the fastener is threadedly secured to the jawbone at the other end.

4. The method of claim 1 wherein the fastener is threadedly secured to the jawbone at the other end.

* * * * *

UNITED STATES PATENT OFFICE
CERTIFICATE OF CORRECTION

PATENT NO. : 4,084,318
DATED : April 18, 1978
INVENTOR(S) : Charles M. McEachern It is certified that error appears in the above-identified patent and that said Letters Patent are hereby corrected as shown below:

In the heading, change "Michigan" to -- Mississippi --.

Signed and Sealed this

Fifteenth Day of August 1978

[SEAL]

Attest:

RUTH C. MASON
Attesting Officer

DONALD W. BANNER
Commissioner of Patents and Trademarks